US007004919B2

(12) United States Patent
Gaylord et al.

(10) Patent No.: US 7,004,919 B2
(45) Date of Patent: Feb. 28, 2006

(54) PATELLA STABILIZING KNEE BRACE

(75) Inventors: Eric Lee Gaylord, Matthews, NC (US); Robert Scott Gaylord, Matthews, NC (US)

(73) Assignee: Medical Specialties, Inc., Charlotte, NC (US)

( * ) Notice: Subject to any disclaimer, the term of this patent is extended or adjusted under 35 U.S.C. 154(b) by 393 days.

(21) Appl. No.: 10/624,065

(22) Filed: Jul. 21, 2003

(65) Prior Publication Data
US 2005/0020951 A1    Jan. 27, 2005

(51) Int. Cl.
*A61F 5/00* (2006.01)

(52) U.S. Cl. .............................. 602/62; 602/60; 602/61; 602/23; 602/26; 128/882

(58) Field of Classification Search ............... 602/5, 602/6, 23, 26, 60, 61, 62, 63; 2/22, 24, 911; 128/882, 892
See application file for complete search history.

(56) References Cited

U.S. PATENT DOCUMENTS

| 2,195,024 | A | * | 3/1940 | Bullock ................... 602/26 |
| 2,270,685 | A | | 1/1942 | Miller |
| 3,804,084 | A | * | 4/1974 | Lehman ................... 602/26 |
| 4,296,744 | A | | 10/1981 | Palumbo |
| 4,986,263 | A | | 1/1991 | Dickerson et al. |
| 5,016,621 | A | * | 5/1991 | Bender ................... 602/26 |
| 5,024,216 | A | | 6/1991 | Shiono |
| 5,277,697 | A | | 1/1994 | France et al. |
| 5,399,153 | A | * | 3/1995 | Caprio et al. ............. 602/26 |
| 5,472,413 | A | * | 12/1995 | Detty ..................... 602/26 |
| 5,513,658 | A | * | 5/1996 | Goseki ................... 128/882 |
| 5,613,943 | A | | 3/1997 | Palumbo |
| 5,759,167 | A | | 6/1998 | Shields, Jr. et al. |
| 5,807,298 | A | | 9/1998 | Palumbo |
| D404,819 | S | | 1/1999 | Rodgers |
| 5,865,776 | A | | 2/1999 | Springs |
| 5,873,848 | A | | 2/1999 | Fulkerson |
| 5,944,682 | A | | 8/1999 | Milana-Panopoulos |
| 6,287,269 | B1 | | 9/2001 | Osti et al. |
| 6,551,264 | B1 | * | 4/2003 | Cawley et al. ............. 602/16 |
| 2002/0147422 | A1 | | 10/2002 | Darcey et al. |
| 2004/0153017 | A1 | * | 8/2004 | Simmons et al. ........... 602/26 |

FOREIGN PATENT DOCUMENTS

| EP | 0 010 389 | 4/1980 |
| EP | 0 115 029 | 8/1984 |

(Continued)

Primary Examiner—Henry Bennett
Assistant Examiner—Amanda Wieker
(74) Attorney, Agent, or Firm—Summa, Allan & Additon, P.A.

(57) ABSTRACT

An apparatus for stabilizing movement of the patella in the patellofemoral joint comprises in one embodiment a base having an opening, a buttress secured to the base sheet member, a tensioning member secured to the base sheet member, a pair of tensioning arms secured to the buttress, a pair of tensioning arms secured to the tensioning member, a pair of compression members formed from the base, and a stabilizing member secured to an edge of the base. A method of stabilizing movement of the patella in the patellofemoral joint during physical activities comprises in one embodiment the steps of positioning a support brace having an opening against the knee, extending a portion of the brace against the knee to apply a first force against portions of the knee in the opening, and extending another portion of the brace against the knee to apply a second force against the knee.

47 Claims, 3 Drawing Sheets

FOREIGN PATENT DOCUMENTS

| | | |
|---|---|---|
| FR | 2 606 998 | 11/1986 |
| GB | 2 136 294 A | 9/1984 |
| GB | 2 279 255 A | 1/1995 |
| WO | WO 92-03110 | 3/1992 |

* cited by examiner

PATELLA STABILIZING KNEE BRACE

FIELD OF THE INVENTION

The invention relates to an apparatus for stabilizing movement of the patella. In particular, the invention relates to an apparatus for stabilizing movement of the patella in the patellofemoral joint while permitting flexion of the knee during physical activities. The invention further relates to a method for stabilizing movement of the patella in the patellofemoral joint during physical activities.

BACKGROUND OF THE INVENTION

As known to those skilled in the art, the knee is one of the most used and abused joints in the body. An individual uses the knee joint over one million times per year. As a result of such use, the knee is one of the most injured joints in the body. The knee is more vulnerable to injury because it is one of the most mobile and flexible joints. The more mobile a joint, the less stable the joint; thus, the more vulnerable the joint is to injury.

The knee is not only the largest joint in the body, but is also one of the most complex. The knee joint is comprised of four bones—the femur, tibia, fibula, and patella—that provide smooth, stable motion. The femur or thighbone is the large bone in the thigh. The tibia or shinbone is the large shinbone. The fibula is the small shinbone located next to the tibia. The patella or kneecap is the small bone in the front portion of the knee. Muscles, ligaments, and tendons connect all four of the above referenced bones.

The four bones of the knee joint are enclosed in a joint capsule lined with a special tissue called synovium, which produces a thick liquid called synovial fluid. The synovial fluid lubricates, protects, and nourishes the joint. The knee is kept in alignment by ligaments and tendons. The ligaments connect the bones and provide stability to joints. There are four main ligaments in the knee joint—anterior cruciate ligament (ACL), the posterior cruciate ligament (PCL), the medial collateral ligament (MCL), and lateral collateral ligament (LCL).

The ACL and PCL are paired ligaments located in the center of the knee where the ACL crosses in front of the PCL. Thus, the ACL and PCL are referred to as the cruciate ligaments. The ACL and PCL prevent the tibia from moving forward and backward on the femur. The ACL originates near the back or posterior aspect of the thighbone and ends at the front or anterior aspect of the knee. In contrast, the PCL starts from the front or anterior aspect of the thighbone and ends at the back or posterior aspect of the knee.

The MCL is located on the inner or medial aspect of the knee and the LCL is located on the outer or lateral aspect of the knee. The MCL and LCL are also referred to as the collateral ligaments. The MCL and LCL supply stability when the knee moves from side to side or when an individual makes any sharp cutting moves.

Two semicircular rings of cartilage called menisci are located between the femur and tibia. Menisci supply additional stability to the knee when the knee twists or pivots. The inside or medial meniscus is also partially attached to the MCL. Accordingly, injury to the MCL leads to injury of the medial menisci, and vice versa. In contrast to the medial aspect of the knee, the outside or lateral meniscus is not attached to the collateral ligaments. Thus, injury to the MCL rarely leads to injury of the lateral meniscus and vice versa.

The knee also includes the patellar tendon and the quadriceps tendon. These tendons are connected to the patella. The patellar tendon—located below the patella—is a rope-like structure that connects the bottom of the patella to the top of the tibia. The quadriceps tendon is located above the patella. The quadriceps muscles straighten the knee by pulling at the patellar tendon via the patella. One of the quadriceps muscles, the vastus medialis, pulls the patella inward (i.e., medially). Another quadriceps muscle, the vastus lateralis, pulls the patella outward (i.e., laterally). Ligaments on the medial and lateral sides of the patella work with the quadriceps muscles to help keep the patella from moving out of a groove in the femur that is referred to as the femoral trochlea or trochlear groove.

The patella slides up and down in the groove as the knee bends and straightens. The patella has a smooth coating (i.e., articular cartilage) on its underside that permits the patella to slide easily in this groove. The trochlear groove is also coated with articular cartilage. Movement of the patella outside of trochlear groove can result in a subluxation when the patella moves partially out of and back into the groove, or a total patellar dislocation when the patella moves completely out of the groove and remains so.

Patellar subluxations are referred to as mild dislocations. Typically, the patella dislocates or subluxes laterally. The medial patellar ligament and the vastus medialis oblique muscle are important structures in preventing the patella from subluxing or dislocating laterally. When the patella subluxes or dislocates laterally, the medial patellar ligament and the vastus medialis muscle are usually damaged. One or more patellar subluxations or dislocations may cause the knee to feel unstable. This type of problem is referred to as patellar instability. This instability occurs because the muscles and ligaments are unable to keep the patella in the trochlear groove. Dislocation is the most severe form of patellar instability. Thus there is a need for a support brace that is capable of stabilizing patellar movement and restricting movement of the patella out of the trochlear groove.

Patellar dislocation may be classified as traumatic or atraumatic. Traumatic patellar dislocation is typically caused by an accident (e.g., a sudden twisting of the knee caused the patella to move out of the groove. In these cases, a ligament is typically torn and may never properly heal, thus leading to recurring knee problems.

Atraumatic patellar dislocation refers to the situation where there was no specific injury before the patella began moving out of the groove. Atraumatic patellar dislocation is common in individuals that are "loose-jointed." It is also common in individuals having a misaligned patella (i.e., tilted or shifted) that places them at risk for instability.

Initially, individuals who dislocate their patella complain of sudden pain in their knee after a plant and twist type of injury or after a contact injury. Straightening the knee will oftentimes cause the patella to move back into the trochlear groove. Nevertheless, if the patella remains out of the groove, a specialist is often required to reposition it in the groove.

Patellar instability does not always lead to subluxation or dislocation. In situations where the kneecap shifts, but never actually dislocates, the condition can be limited to pain around the kneecap. Those skilled in the art refer to this condition as "excess lateral pressure syndrome" or "lateral tracking." This type of pain typically occurs on the outside of the patella. Therefore, it is desirable to provide a support brace that facilitates proper tracking of the patella in the patellofemoral joint to thereby alleviate pain caused by improper tracking.

Patellofemoral pain can occur in one or both knees and is one of the most common causes of knee pain. Patellofemoral pain typically occurs in the front of the knee and occurs when the patella is compressed against the trochlear groove. The compression forces increase the further the knee is bent, resulting in an increase in pain. Therefore, activities that involve repetitive bending of the knee increase patellofemoral pain. Pain is often felt by the individual when moving up or down stairs or after sitting for long periods of time. Patellofemoral pain may also be accompanied by "clicking" and "grinding" or by a feeling that the knee "catches" in the patellofemoral joint. Thus, it is further desirable to provide a support brace that stabilizes movement of the patella in the patellofemoral joint, while permitting flexion of the knee during physical activities such as basketball or football.

Patellofemoral pain describes the location of the pain but not its cause. Overuse or previous injury to the knee is a common cause of patellofemoral pain. Biomechanical factors such as poor tracking of the patella in the trochlear groove, pronated feet, weak inner thigh muscles, and tight outer thigh muscles or ligaments can also cause patellofemoral pain. Common "wear and tear arthritis" (i.e., osteoarthritis) or damage to the articular cartilage (i.e., chondromalacia) on the back of the patella is another common cause of pain. Those suffering from patellofemoral pain often resort to knee support braces to prevent improper tracking of the patella and to alleviate the associated pain.

Bracing centralizes the patella in the trochlear groove such that it tracks more centrally, thereby decreasing pain. As mentioned above, the patella usually subluxes or dislocates laterally. Thus, most braces include a buttress positioned laterally to push the patella medially. Nevertheless, the patella may also sublux or dislocate medially. Thus it is desirable to provide a support brace having a buttress that is capable of applying sufficient lateral or medial forces against either knee to ensure proper tracking of the patella in the patellofemoral joint.

Patellar stabilizing braces are designed to reduce knee instability following a patellar dislocation or subluxation. They are usually recommended for twisting, pivoting, cutting, or jumping activities. In addition to providing increased stability to the patella, patellar stabilizing braces may also decrease the risk of injuring other parts of the knee. Thus, it is desirable to provide a support brace having a buttress that is capable of applying sufficient forces against the knee to ensure proper tracking of the patella in the patellofemoral joint.

Known braces provide at least one member (e.g., strap or buttress) for applying force against the knee, and specifically, the patella. The known buttresses, however, tend to shift during physical activities as a result of the relatively small areas of attachment to the brace body (i.e., relatively small attachment points provided by elongate arms). Thus it is desirable to provide a brace having a buttress that is secured in position by a second member (e.g., sheet-like member) that overlies at least a portion of the buttress and provides additional points of attachment to the brace body, thereby providing greater stability to the buttress.

Know braces also have a tendency to shift when the user applies tension to the buttress prior to attachment to the brace body. Therefore it is desirable to provide a brace having a stabilizing member for the user to grasp when applying tension to the buttress or additional tensioning members, to thereby secure the position of the brace and buttress relative to the knee when extending the brace against the knee.

OBJECT AND SUMMARY OF THE INVENTION

It is therefore an object of the present invention to provide a support brace that is capable of stabilizing patellar movement and restricting movement of the patella out of the trochlear groove.

Another object of the invention is the provision of a support brace that facilitates proper tracking of the patella in the patellofemoral joint to thereby alleviate pain caused by improper tracking.

A further object of the invention is to provide a support brace that stabilizes movement of the patella in the patellofemoral joint, while permitting flexion of the knee during physical activities.

Still another object of the invention is to provide a support brace having a buttress that is capable of applying sufficient lateral or medial forces against either knee to ensure proper tracking of the patella in the patellofemoral joint.

Still another object of the invention is to provide a support brace having a buttress that is capable of applying sufficient forces against the knee to ensure proper tracking of the patella in the patellofemoral joint.

Another object of the invention is to provide a brace having a buttress that is secured in position by a second member, to thereby provide greater stability to the buttress.

Still yet another object of the invention is provide a brace having a stabilizing member for the user to grasp when applying tension to the buttress or additional tensioning members, to thereby secure the position of the brace and buttress relative to the knee when securing the brace to the knee.

The invention meets these objectives with a support brace that is capable of stabilizing movement of the patella in the knee. In particular, the invention is a support brace having a base defining an opening for receiving portions of the knee, a buttress covering a portion of the opening for applying a first force against the knee, a tensioning member covering the buttress and a portion of the opening for applying a second force against the knee in addition to the first force applied by the buttress, and a stabilizing member for preventing movement of the brace and buttress relative to the knee when the first and second forces are applied against the knee.

The foregoing and other objects and advantages of the invention and the manner in which the same are accomplished will become clearer based on the following detailed description taken in conjunction with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Those skilled in the art will also appreciate that the term "adjacent" refers to two or more, for example, elements, that have a common border or are in close proximity to one another. Nevertheless, it will be understood that adjacent may or may not imply contact, but always implies the absence of anything of the same kind in between.

It will also be appreciated that the term "secured" may include sewn, made integral with, adhered with adhesive, sonically welded, or bonded with heat.

Figure 1:
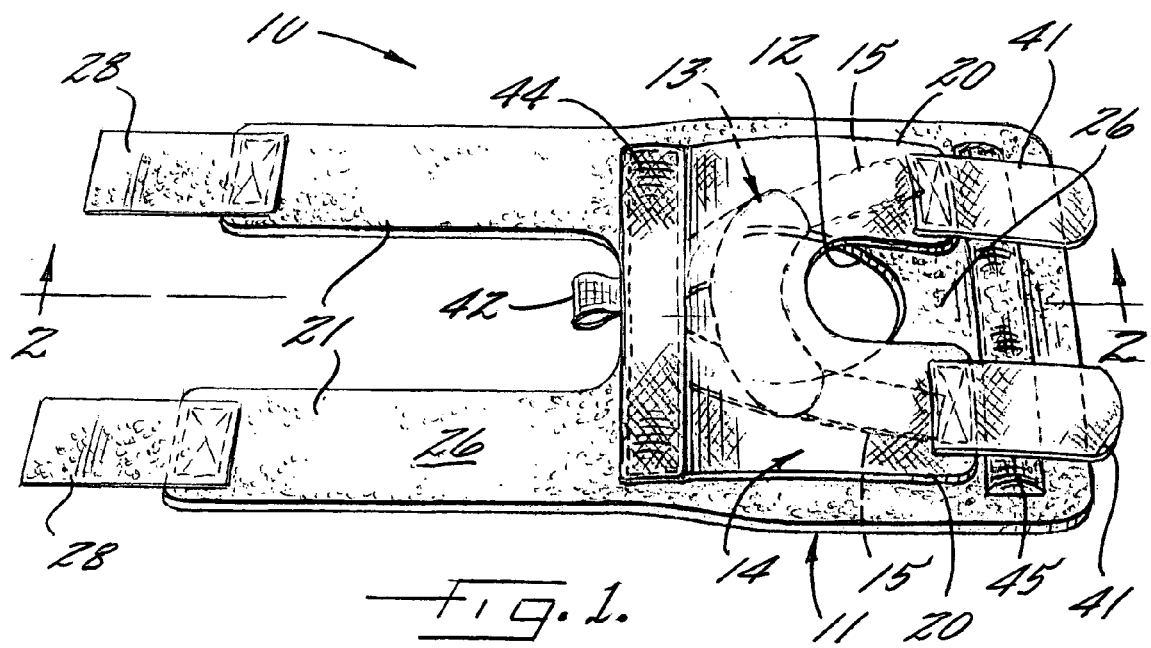
FIG. 1 is a perspective view of a preferred embodiment of a brace depicting a base having an opening, a buttress in an extended position, a pair of tensioning arms secured to the buttress, a tensioning member in the extended position, a pair of tensioning arms secured to the tensioning member, a stabilizing member, and a pair of compression members.
Figure 2:
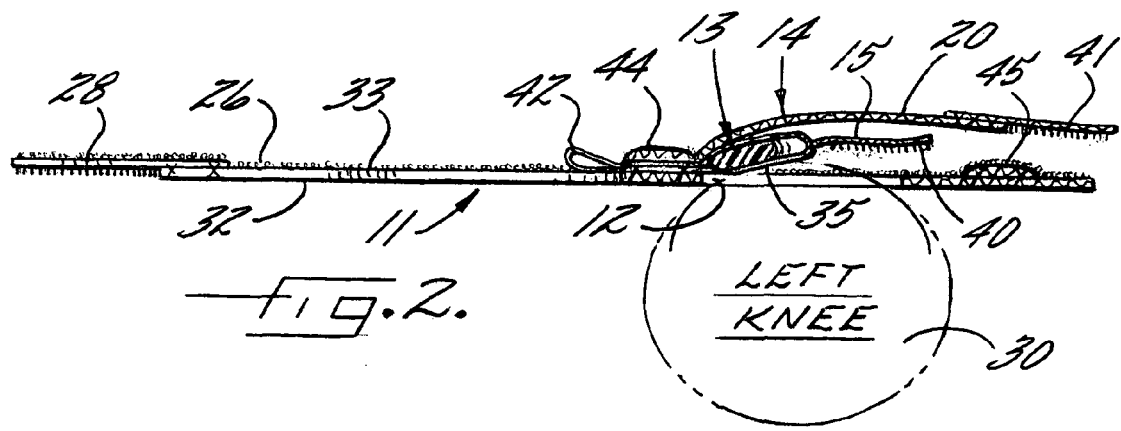
FIG. 2 is a side elevation view of a preferred embodiment of the brace depicting the buttress and tensioning member extended across the opening and against portions of a knee positioned in the opening.

Referring to FIG. 1, it will be understood that the term "portion" refers to various areas of the brace. It will be further understood by those skilled in the art that the terms "upper portion" and "lower portion", and "right portion" and "left portion", may also refer to "lower portion" and "upper portion," and "left portion" and "right portion," respectively, dependent upon the perspective of the individual viewing the apparatus. It will also be appreciated that the term "upper" implies the "opposite" of lower, and term "right" implies the opposite of "left."

As used herein, it will be understood that the term "elastic" refers to material that is capable of being easily stretched or expanded and resuming its former shape. Stated differently, the term elastic implies the property of resisting deformation by stretching. In a related aspect, it will be understood by those skilled in the art that "elastomers" are a group of polymers that can easily undergo very large, reversible elongations at relatively low stresses. Accordingly, the term "elastomeric" describes the characteristic of a material formed from elastomers.

It will also be understood by those of skill in the art that as used herein, the concept of an element being "between" two other elements does not necessarily imply that the three elements are contiguous (i.e., in intimate contact). Rather, as used herein, the concept of one element being between two other elements is meant to describe the relative positions of the elements within the brace structure, respectively.

Those of skill in the art will further understand that the phrase "extended against the knee" means the act of wrapping the brace around the knee joint.

With reference to the opening in the apparatus, those skilled in the art will understand that the term "side" refers to the areas adjacent the opening and extending outward there from in any number of directions.

Figure 6:
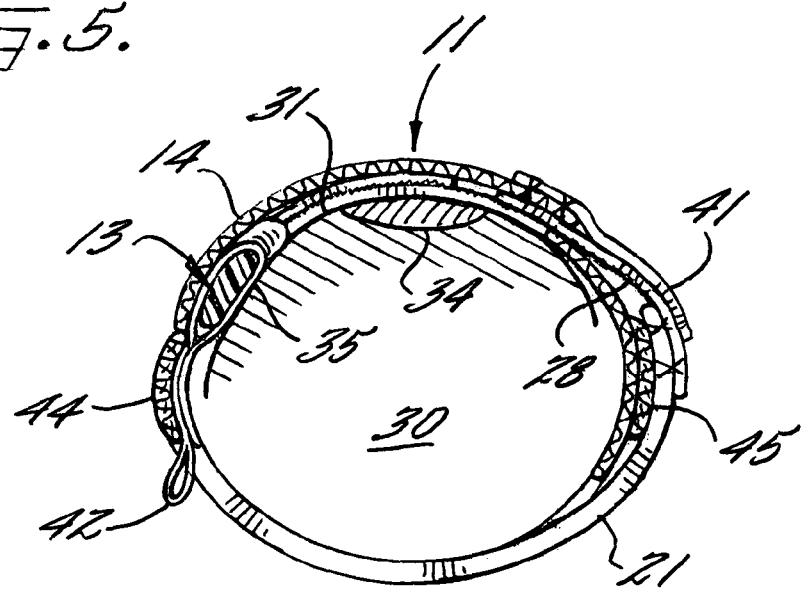
FIG. 6 is a top planar view of a preferred embodiment of the brace extended against the knee taken along lines 6—6 of FIG. 5 illustrating the base, the buttress extended against the knee and removably attached to portions of the base, the tensioning member extended against the knee and removably attached to the base, and the pair of compression members extended and removably attached to the base.

With reference to the orientation of the brace in FIGS. 1 and 6, it will be understood by those of skill in the art that the terms "top side" and "bottom side", are also referred to as "external side" and "internal side", dependent upon whether the brace is standing alone or is extended against the knee. See FIGS. 1 and 6, respectively.

An overall view of a preferred embodiment of a support brace 10 which incorporates features of the present invention is set forth in FIG. 1. As depicted in FIG. 1, the support brace 10 includes a base sheet member or base 11 having at least one opening 12, a buttress 13 secured to the base, a tensioning sheet or tensioning member 14 secured to the base and overlying the buttress, a pair of buttress tensioning arms 15 secured to the buttress, a pair of tensioning member tensioning arms 20 secured to the tensioning member, and a pair of compression members 21. It will be understood that the joint 30 against which the brace 10 is extended is preferably a knee, such that the buttress 13 and the tensioning member 14 stabilize patellar movement.

The base 11 includes an upper portion 22, a lower portion 23, a right portion 24, and a left portion 25. In a preferred embodiment, the base 11 is flexible and includes a patterned surface 26 to facilitate engagement with other portions of the base when extended against the knee 30. For example, the patterned surface 26 of the base 11 may be formed from a plurality of fasteners such as loops for engaging hooks secured to other portions of the brace 10. In a more preferred embodiment, the base 11 is formed from elastomers. Stated differently, the more preferred embodiment of the invention is made from elastomeric material (e.g., neoprene) or any variety of elastic substances resembling rubber (e.g., polyvinyl elastomers). The preferred material of the base 11 may be knitted or woven material.

The opening 12 defined by the base 11 is configured to receive portions of a joint 30 (e.g., a knee) when the base is extended against the joint. The opening 12 is preferably positioned to receive at least a portion of a patella 31.

The base 11 includes an internal or bottom planar side 32 and an external or top planar side 33. As used herein, the term internal planar side 32 refers to the portion of the base 11 that contacts tissue when the support brace 10 is extended against the knee 30 and the external planar side 33 refers to the opposite side. Accordingly, the term bottom planar side 32 refers to the portion of the support brace 10 contacting a surface when standing alone as depicted in FIG. 1. The term top planar side 33, thus, refers to the side opposite the bottom planar side 32. The internal planar side 32 of the base 11 may include a tissue contact patch 34 positioned at the upper or lower portions 22, 23 of the base 11 adjacent the opening 12. See FIG. 6. The tissue contact patch 34 may include synthetic leather or any other material having a sufficient coefficient of friction with respect to tissue to prevent movement of the base 11 on the limb and limit distal migration of the brace 10.

As described above, the patterned surface 26 forming the external or top planar side 33 of the base 11 is preferably formed by fasteners for removably attaching portions of the base 11, the buttress 13, and the tensioning member 14 to at least a portion of the external planar side of the base. In a preferred embodiment, the fasteners 26 may include hook and loop fasteners. More specifically, the fasteners 26 removably attach the pair of buttress tensioning arms 15, the pair of tensioning member tensioning arms 20, and the pair of compression members 21 to a portion of the external planar side 33 of the base 11. As configured, portions of the base 11 are foldable against and removably fixed to one another to define a sleeve capable of applying a compressive force against the joint 30. See FIG. 6.

The buttress 13 is designed to cover at least a portion of the opening 12. The buttress 13 is secured to the base 11 adjacent the opening 12 and proximate the joint 30 for applying a first force $F_1$ against those sections of the joint in the opening. See FIG. 4C. Stated differently, a portion of the buttress 13 is fixed against one side of the opening 12 in the base 11 and at least one other portion of the buttress is removably attachable to the base at the opposite side of the opening. Accordingly, a portion of the buttress 13 is removably attachable to a portion of the base 11 opposite the portion to which the buttress is secured.

A preferred embodiment of the invention includes a padded buttress 13 that is substantially arcuate in shape and positioned concave with respect to the opening 12. Advantageously, buttress 13 has a tissue contact surface 35 formed from material that restricts movement of the buttress relative to the tissue when the buttress is extended across the opening 12 and removably attached to the base 11. The tissue contact surface 35 may include a patch of synthetic leather or any other material having a sufficient coefficient of friction with respect to tissue to prevent movement of the buttress 13 and limit distal migration of the brace 10.

In a preferred embodiment, the tensioning member 14 is flexible and is formed from elastomeric material. The tensioning member 14 covers the buttress 13 and portions of the opening 12, to thereby further secure the buttress against the patella 31 to ensure proper tracking. The tensioning member 14 is secured to the base 11 adjacent the buttress 13 and proximate the joint 30 for applying a second force $F_2$ against the joint in addition to the first force $F_1$ applied by the buttress. See FIG. 4D. Specifically, a portion of the tensioning member 14 is fixed to the base 11 adjacent the opening 12 and another portion of the tensioning member is removably attachable to the base at the opposite side of the opening. Stated differently, a portion of the tensioning member 14 is removably attachable to a portion of the base 11 opposite the portion to which the tensioning member is secured. A preferred embodiment of the buttress 13 and tensioning member 14 are removably attachable to the base 11 with hook and loop fasteners 40, 41.

Figure 4:
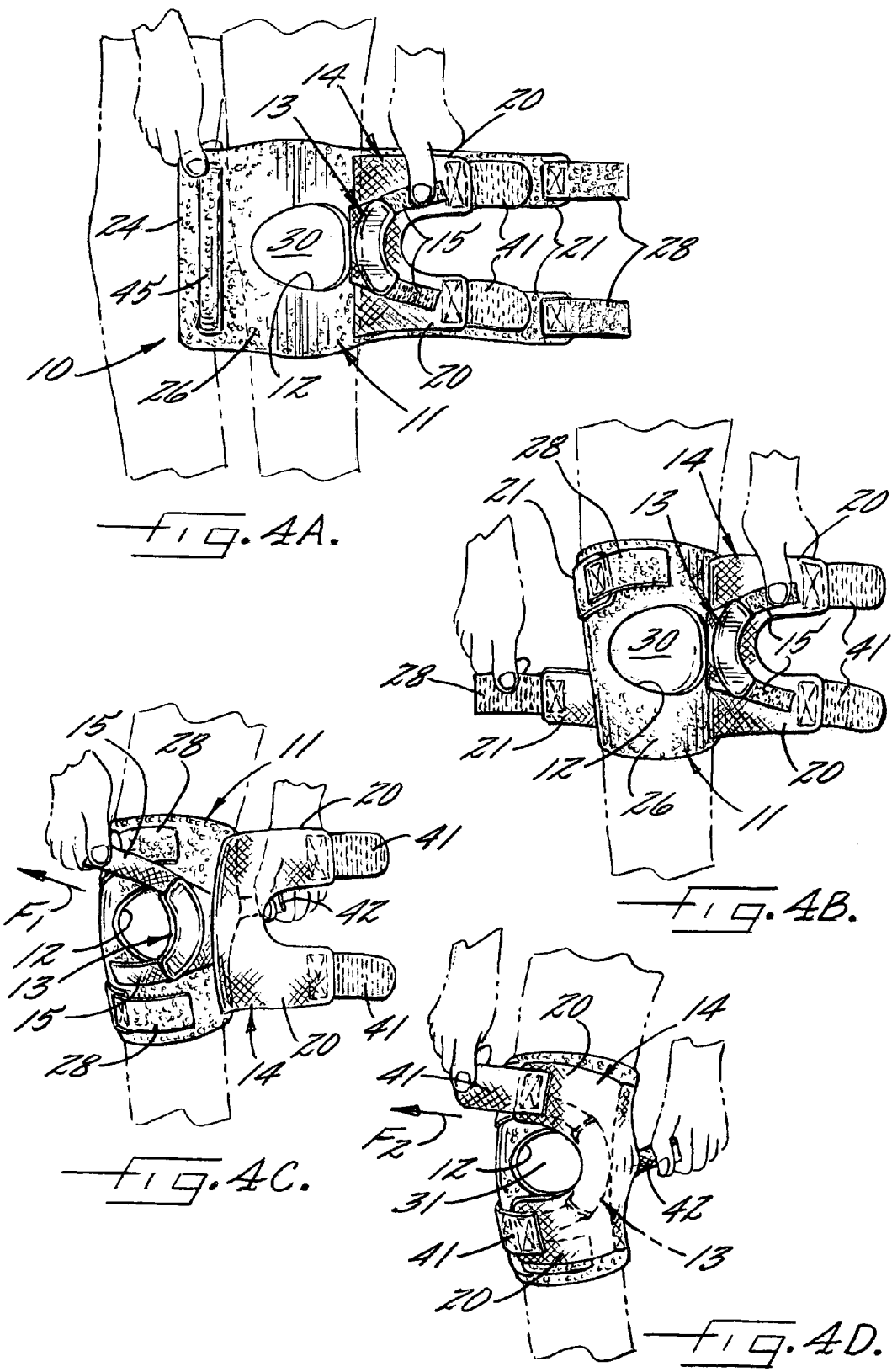
FIGS. 4A–4D are perspective views of a method for stabilizing movement of the patella that incorporates a preferred embodiment of the brace.

The support brace 10 includes at least one, and preferable a pair, of tensioning arms 15 secured to the portion of the buttress 13 that is removably attachable to the base 11. The buttress tensioning arms 15 are removably attachable to a side of the opening 12 to thereby attach a portion of the buttress 13 to the base 11. Stated differently, the tensioning arms 15 are secured to a portion of the buttress 13 opposite the portion secured to the base 11. The buttress tensioning arms 15 are removably attachable to the base 11 for selectively applying the first force $F_1$. Further, the pair of buttress tensioning arms 15 facilitates the application of force vectors against the knee 30 in selectable angular orientations. As depicted in FIG. 4C, the buttress tensioning arms 15 extend from the ends of the buttress 13 in a Y-like pattern. When extended against the patella 31, the buttress tensioning arms 15 are preferably attached to an upper side and lower side of the opening 12 in the base 11 opposite the side to which the buttress 13 is fixed. The buttress tensioning arms 15 extend in directions substantially divergent from one another relative to the buttress 13 when removably attached to the base 11. Advantageous to this configuration, the buttress tensioning arms 15 increase the amount of the first force $F_1$ applied against the patella 31 during flexion of the knee 30 because the arms are stretched during flexion of the knee. Stated differently, flexion of the knee 30 stretches the base 11 and increases the distances between the points of attachment of the arms 15 (i.e., attachment point to the buttress 13 and attachment point to the base).

The support brace 10 also includes at least one, and preferably a pair, of tensioning arms 20 secured to the portion of the tensioning member 14 that is removably attachable to the base 11. The tensioning member tensioning arms 20 are of sufficient length to cover the opening 12 and buttress 13. The tensioning arms 20 are secured to a portion of the tensioning member 14 opposite the portion secured to the base 11. The tensioning member tensioning arms 20 are removably attachable to the base 11 for selectively applying the second force $F_2$. The tensioning member tensioning arms 20 likewise provide force vectors in selectable angular orientations.

Figure 3:
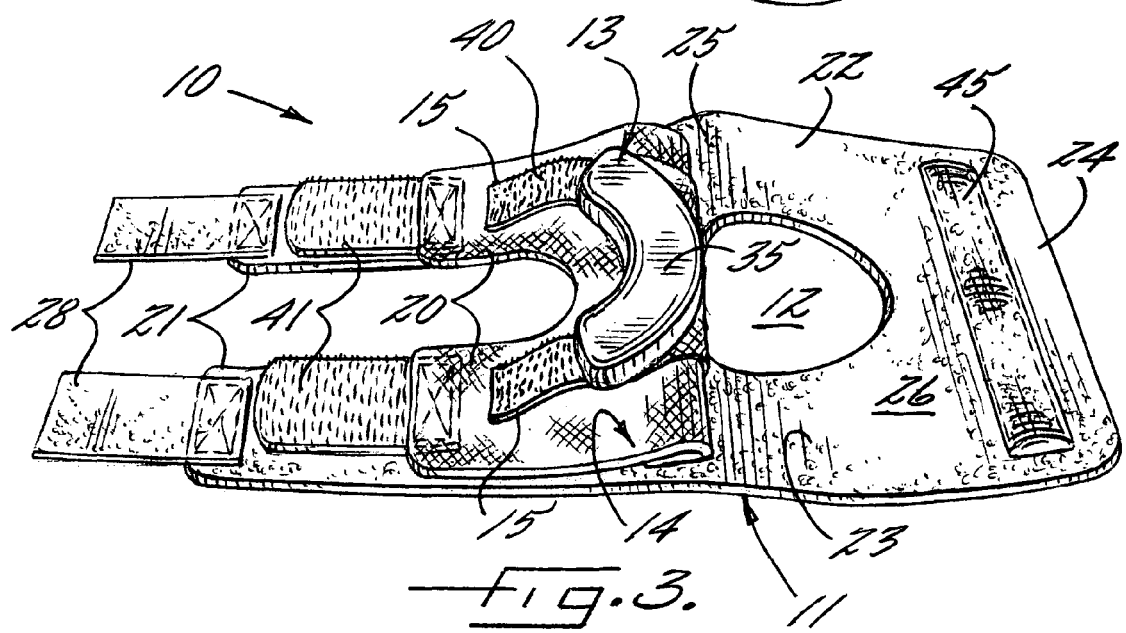
FIG. 3 is a perspective view of a preferred embodiment of the brace illustrating the buttress and tensioning member in an open or non-extended position.

As illustrated in FIG. 3, buttress tensioning arms 15 and the tensioning member tensioning arms 20 preferably include fasteners 40, 41 (e.g., hook and loop fasteners) for removably attaching portions of the buttress 13 and tensioning member 14 to the base 11.

Advantageously, the first force $F_1$ applied by the buttress 13 and the second force $F_2$ applied by the tensioning member 14 are co-directional and cumulative. As configured, the support brace 10 can be extended or wrapped against either knee 30 such that the buttress 13 and tensioning member 14 apply either lateral or medial forces against either the left or right patella 31. In other words the brace 10 can be fitted against either knee 30 and positioned such that the buttress 13 is to the left or right of the user's patella 31. Accordingly, the brace 11 may be positioned against the knee 30 such that the first force $F_1$ applied by the buttress 13 and the second force $F_2$ applied by the tensioning member 14 are medial forces or lateral forces.

A stabilizing member 42 is provided to assist in the stabilization of the brace 10 upon extension against the joint 30. In a preferred embodiment, the stabilizing member 42 is a looped tab made of cloth or any other type of non-elastic material. The stabilizing member 42 has one end fixed to the base 11 adjacent the tensioning member 14 and another end that is free. The stabilizing member 42 is configured to prevent movement of the base 11 and the buttress 13 relative to the joint 30 when the buttress and the tensioning member 14 are extended across portions of the opening 12. Specifically, the user extends the base 11 against the knee 30 and around the joint, and secures portions of the brace 10 together to form a sleeve. Next, the user grasps and holds the stabilizing member 42 while pulling the buttress 13 against the patella 31 and pulling the tensioning member 14 across the buttress 13 and opening 12.

Figure 5:
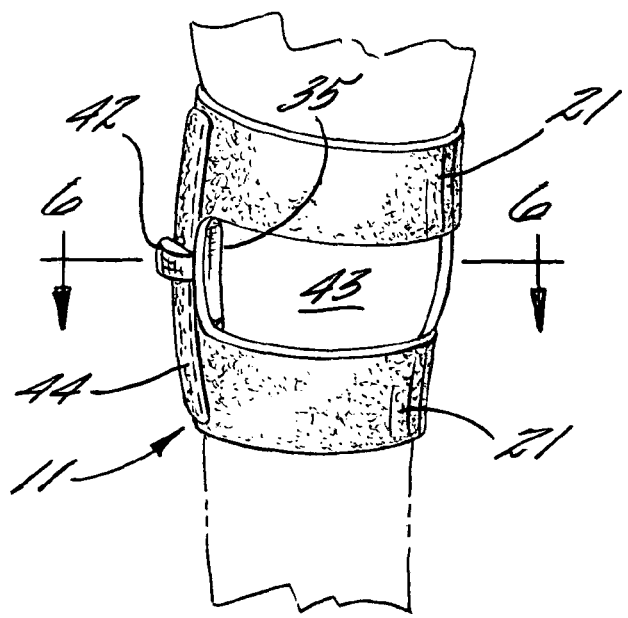
FIG. 5 is a perspective view of a preferred embodiment of the brace as extended against the posterior portion of a knee depicting the pair of compression members and the stabilizing member.

In a preferred embodiment, the base 11 includes at least one, and preferably a pair, of spaced apart elongate compression members 21 that extend laterally from the portion of the base to which the tensioning member 14 is secured. The compression members 21 are of sufficient length to extend around the knee 30 and removably attach to the base 11 for selectively applying a compressive force against the knee. The compression members 21 include fasteners 28 (e.g., hook and loop fasteners) that removably attach the members to the external planar side 33 of the base 11. Upon securing the support brace 10 to the knee 30, the compression members 21 define a popliteal opening 43 adjacent the posterior portion of the knee. See FIG. 5.

A preferred embodiment of the invention also includes a first and second elongated rib 44, 45 secured to the base 11 on opposite sides of the opening 12. The elongated ribs 44, 45 provide additional support against impacts to the knee 30 during athletic activities. With reference to the orientation of the support brace 10 in FIG. 3, the ribs 44, 45 are positioned substantially parallel to one another and extend from an upper portion 22 of the base 11 to a lower portion 23 of the base. Specifically, the first rib 44 is secured to the base 11 adjacent the tensioning member 14 such that the first rib 44 is positioned between the opening 12 and the stabilizing member 42 (or on the left side of the opening). The second rib 45 is secured to the base 11 adjacent the opening 12 such that the second rib is positioned between the opening and an edge of the base that is opposite the edge to which the stabilizing member 42 is fixed (or on the right side of the opening and adjacent the right edge of the base).

Another aspect of the invention includes the use of the support brace 10 of the present invention in conjunction with a method for stabilizing movement of the patella 31 in the patellofemoral joint, while permitting flexion of the knee 30 during physical activities. See FIGS. 4A–4D.

In a preferred method, the support brace 10 is positioned against either knee 30—e.g., the left knee as depicted in FIG. 4A—such that at least a portion of the knee is positioned in the opening 12. Specifically, the compression members 21 of the brace 10 are wrapped around the knee 30 such that the opening 12 receives the patella 31. The user then removably fixes portions of the brace 10 to one another to form a sleeve around the knee. See FIGS. 4B and 6. Once secured, the brace 10 applies a compressive force about portions of the knee joint 30 surrounded by the brace (i.e., the superior, inferior, anterior, and posterior portions immediately adjacent the knee joint).

With reference to FIG. 4C, the user then secures the brace 10 by grasping the stabilizing member 42 fixed to an edge of the brace to thereby prevent movement of the brace and buttress 13 relative to the knee 30 in preparation for the application of the first and second forces $F_1$, $F_2$.

Still referring to FIG. 4C, the user next extends the buttress 13 against the knee 30 to apply a first force $F_1$ against portions of the knee in the opening 12 (i.e., the patella 31). Specifically the user extends the pair of buttress tensioning arms 15 across at least a portion of the opening 12 and against the patella 31. The user then removably attaches the buttress 13, and specifically the ends of the buttress tensioning arms 15, to the base 11 of the brace 10. The user attaches the buttress tensioning arms 15 to an opposite side of the opening 12 such that the buttress 13 covers at least a portion of the knee (i.e., patella 31) in the opening.

Advantageously, the user is able to selectively apply the first force $F_1$ against the patella 31 by adjusting the tension on each one of the buttress tensioning arms 15 before removably attaching the ends of the arms to the base 11. See FIG. 4C. In a further advantage provided by the present invention, the stabilizing member 42 is provided so that the user is able to secure the buttress 13 and brace 10 relative to the knee 30 when selectively applying the first force $F_1$ as well as the second force $F_2$, as discussed herein.

Upon securing the buttress 13 against the patella 31 and to the brace 10, the user then extends another portion of the brace against the knee 30 to apply a second force $F_2$ against the patella. See FIG. 4D. In particular, the user extends the pair of tensioning member tensioning arms 20 across at least a portion of the opening 12 and against the buttress 13. Referring to FIG. 4D, the user next removably attaches the tensioning member 14, and specifically, ends of the tensioning member tensioning arms 20, to the brace 10 (i.e., base 11). The user attaches the tensioning member tensioning arms 20 to an opposite side of the opening 12 such that the tensioning member 14 overlies the buttress 13 and a portion of the opening. The user likewise selectively applies the second force $F_2$ against the knee 30, and specifically the patella 31, by adjusting the tension on each one of the tensioning member tensioning arms 20 before removably attaching the ends of the arms to the base 11. As noted above, the stabilizing member 42 permits the user to secure the buttress 13 and brace 11 relative to the knee 30 when selectively applying the second force $F_2$ as well as the first force $F_1$.

The preferred method used in connection with the preferred embodiment of the invention facilitates the application of first and second forces $F_1$, $F_2$ that are co-directional and cumulative. Further, the preferred method incorporating the preferred design of the invention permits the user to apply first and second forces $F_1$, $F_2$ that are lateral or medial with respect to the knee 30.

In the drawings and specification, there have been disclosed typical embodiments on the invention and, although specific terms have been employed, they have been used in a generic and descriptive sense only and not for purposes of limitation, the scope of the invention being set forth in the following claims.

That which is claimed is:

1. An apparatus for stabilizing movement of the patella in the patellofemoral joint, while permitting flexion of the knee during physical activities, said apparatus comprising:
   a patterned flexible base sheet member defining at least one opening;
   a padded buttress having one portion fixed against one side of said opening and having at least another portion removably attachable to an opposite side of said opening; and
   a flexible tensioning sheet overlying said padded buttress, said tensioning sheet having one portion fixed to said base sheet member adjacent said opening and having at least another portion removably attachable to said base sheet member at an opposite side of said opening.

2. An apparatus according to claim 1, wherein said flexible base sheet member has a top planar side and a bottom planar side, said top planar side having fasteners for removably attaching at least a portion of said flexible base sheet member, said padded buttress, and said flexible tensioning sheet to at least a portion of said top planar side of said base sheet member.

3. An apparatus according to claim 1, wherein portions of said flexible base sheet member are foldable against and removably fixed to one another to thereby define a sleeve.

4. An apparatus according to claim 1, wherein said flexible base sheet member is formed from an elastomeric material.

5. An apparatus according to claim 1, wherein said flexible tensioning sheet is formed from an elastomeric material.

6. An apparatus according to claim 1, wherein said padded buttress is substantially arcuate and concave with respect to said opening.

7. An apparatus according to claim 1, further comprising:
   at least one tensioning arm secured to the portion of said padded buttress that is removably attachable to a side of said opening; and
   at least one tensioning arm secured to the portion of said flexible tensioning sheet that is removably attachable to said flexible base sheet member.

8. An apparatus according to claim 7, wherein said padded buttress tensioning arm and said flexible tensioning sheet tensioning arm have fasteners for removably attaching at least a portion of said padded buttress and said tensioning sheet to said flexible base sheet member.

9. An apparatus according to claim 1, further comprising a stabilizing member having one end fixed to said flexible base sheet member adjacent said flexible tensioning sheet and having the other end free.

10. A support brace for stabilizing a joint, said brace comprising:
 a base defining an opening for receiving portions of a joint when said base is extended against the joint;
 a buttress covering at least a portion of said opening, said buttress secured to said base adjacent said opening and proximate the joint for applying a first force against those sections of the joint in said opening; and
 a tensioning member covering said buttress and portions of said opening, said tensioning member secured to said base adjacent said buttress and proximate the joint for applying a second force against the joint in addition to the first force applied by said buttress;
 wherein said base has an internal planar side and an external planar side, said external planar side having fasteners for removably attaching at least a portion of said base, said buttress, and said tensioning member to at least a portion of said external planar side of said base.

11. A support brace according to claim 10, wherein portions of said base are foldable against and removably fixed to one another to define a sleeve that wraps around the joint.

12. A support brace according to claim 10, wherein said buttress is arcuate and positioned concave with respect to the joint.

13. A support brace according to claim 10, wherein:
 at least a portion of said buttress is removably attachable to a portion of said base opposite the portion to which said buttress is secured; and
 at least a portion of said tensioning member is removably attachable to a portion of said base opposite the portion to which said tensioning member is secured.

14. A support brace according to claim 13, wherein said buttress and said tensioning member removably attach to said base using hook and loop fasteners.

15. A support brace according to claim 10, wherein the first force applied by said buttress and the second force applied by said tensioning member are co-directional and cumulative.

16. A support brace according to claim 10, wherein the first force applied by said buttress and the second force applied by said tensioning member are medial forces.

17. A support brace according to claim 10, wherein the first force applied by said buttress and the second force applied by said tensioning member are lateral forces.

18. A support brace according to claim 10, wherein said joint is a knee, and said buttress and said tensioning member stabilize patellar movement.

19. A support brace according to claim 10, wherein said base and said tensioning member are formed from an elastomeric material.

20. A support brace according to claim 10, further comprising:
 at least one tensioning arm secured to a portion of said buttress opposite the portion secured to said base, said buttress tensioning arm removably attachable to said base for selectively applying the first force; and
 at least one tensioning arm secured to a portion of said tensioning member opposite the portion secured to said base, said tensioning member tensioning arm removably attachable to said base for selectively applying the second force.

21. A support brace according to claim 10, further comprising a stabilizing member having one end fixed to said base adjacent said tensioning member and having another end free for preventing movement of said base and said buttress relative to the joint when said buttress and said tensioning member are extended across portions of said opening.

22. A support brace according to claim 10, wherein said base includes at least one elongate compression member that extends laterally from the portion of said base to which said tensioning member is secured.

23. A support brace for stabilizing movement of the patella in the patellofemoral joint, while permitting flexion of the knee during physical activities, said brace comprising:
 an elastomeric base defining an opening for receiving at least a portion of the patella when said base is extended against the knee, said base having a pair of spaced apart elongated compression members;
 a substantially arcuate buttress covering at least a portion of said opening, said buttress secured to said base adjacent said opening and proximate the patella for applying a first force against the patella;
 a pair of tensioning arms secured to end portions of said buttress opposite the portion of said buttress secured to said base, said pair of buttress tensioning arms removably attachable to said base for selectively applying the first force;
 an elastomeric tensioning member covering said buttress and portions of said opening, said tensioning member secured to said base adjacent said buttress and proximate the patella for applying a second force against the patella in addition to the first force applied by said buttress;
 a pair of tensioning arms secured to portions of said tensioning member opposite the portion of said first tensioning member secured to said base, said pair of tensioning member tensioning arms removably attachable to said base for selectively applying the second force; and
 a stabilizing member having one end fixed to an edge of said base adjacent said tensioning member and having another end free for preventing movement of said base and said buttress relative to the patella when said buttress and said tensioning member are extended across portions of said opening.

24. An apparatus according to claim 23, wherein said base has an internal planar side and an external planar side, said external planar side having fasteners for removably attaching said pair of buttress tensioning arms, said pair of tensioning member tensioning arms, and said pair of compression members to at least a portion of said external planar side of said base.

25. An apparatus according to claim 24, wherein said base includes a tissue contact patch positioned on said internal planar side adjacent said opening.

26. An apparatus according to claim 24, wherein said pair of buttress tensioning arms, said pair of tensioning member tensioning arms, and said pair of compression members removably attach to said base using hook and loop fasteners.

27. An apparatus according to claim 23, wherein portions of said base are foldable against and removably fixed to one another to thereby define a sleeve.

28. An apparatus according to claim 23, wherein said pair of compression members are of sufficient length to extend around the knee and removably attach to said base for selectively applying a compressive force against the knee.

29. An apparatus according to claim 23, wherein said pair of buttress tensioning arms facilitate the application of force vectors against the knee in selectable angular orientations.

30. An apparatus according to claim 23, wherein said pair of buttress tensioning arms extend in directions substantially divergent from one another relative to said buttress when removably attached to said base to thereby increase the amount of the first force applied against the patella during flexion of the knee.

31. An apparatus according to claim 23, further comprising a first and second elongated rib secured to said base on opposite sides of said opening, said first and second ribs substantially parallel to one another.

32. An apparatus according to claim 31, wherein said first and second ribs extend from an upper portion of said base to a lower portion of said base.

33. An apparatus according to claim 31, wherein:
said first rib is secured to said base adjacent said tensioning member such that said first rib is positioned between said opening and said stabilizing member; and
said second rib is secured to said base adjacent said opening such that said second rib is positioned between said opening and an edge of said base that is opposite the edge to which said stabilizing member is fixed.

34. An apparatus according to claim 23, wherein said stabilizing member is a looped tab.

35. An apparatus according to claim 23, wherein said buttress has a tissue contact surface formed from material that restricts movement of said buttress relative to the tissue when said buttress is extended across said opening and removably attached to said base.

36. A method for stabilizing movement of the patella in the patellofemoral joint, while permitting flexion of a knee during physical activities, the method comprising the steps of:
positioning a support brace having at least one opening for receiving portions of a knee against the knee;
extending a buttress having one portion secured to the brace across at least a portion of the opening and against the knee to apply a first force against portions of the knee in the opening;
removably attaching another portion of the buttress to the brace such that the buttress covers at least a portion of the knee in the opening; and
extending another portion of the brace against the knee to apply a second force against the knee.

37. A method according to claim 36, further comprising securing the brace to prevent movement of the brace and buttress relative to the knee when the first and second forces are applied against the knee, the step of securing performed after the step of positioning the brace and before the step of extending the buttress against the knee to apply a first force.

38. A method according to claim 36, wherein the step of positioning comprises:
wrapping the brace around the knee such that the opening receives the patella; and
removably fixing portions of the brace to one another to form a sleeve around the knee for applying a compressive force against portions of the knee surrounded by the brace.

39. A method according to claim 38, wherein the step of removably fixing comprises applying the compressive force about the superior and inferior portions of the knee.

40. A method according to claim 36, wherein the first step of extending comprises selectively applying the first force against the knee to adjust the desired tension on the knee.

41. A method according to claim 36, wherein the step of extending the buttress comprises extending the buttress against a portion of the patella.

42. A method according to claim 36, wherein the second step of extending comprises selectively applying the second force against the knee to adjust the desired tension on the knee.

43. A method according to claim 36, wherein the second step of extending further comprises:
extending a flexible sheet having one portion secured to the brace across at least a portion of the opening; and
removably attaching another portion of the flexible sheet to the brace such that the sheet overlies the buttress and at least a portion of the opening.

44. A method according to claim 43, wherein the step of extending the flexible sheet comprises extending the sheet against a portion of the patella.

45. A method according to claim 36, wherein the first and second steps of extending comprise applying first and second forces, respectively, that are co-directional and cumulative.

46. A method according to claim 36, wherein the first and second steps of extending comprise applying first and second forces, respectively, that are lateral with respect to the knee.

47. A method according to claim 36, wherein the first and second steps of extending comprise applying first and second forces, respectively, that are medial with respect to the knee.

* * * * *